United States Patent [19]
Luker

[11] Patent Number: 6,103,191
[45] Date of Patent: Aug. 15, 2000

[54] CONTINUOUS FLOW PASTEURIZATION OF SEWAGE SLUDGE

[75] Inventor: Michael A. Luker, Menifee, Calif.

[73] Assignee: Riverside County Eastern Municipal Water District, Perris, Calif.

[21] Appl. No.: 09/206,879

[22] Filed: Dec. 8, 1998

Related U.S. Application Data

[63] Continuation-in-part of application No. 08/792,692, Jan. 29, 1997, Pat. No. 5,888,453.

[51] Int. Cl.[7] ..................................................... A61L 2/00
[52] U.S. Cl. ........................... 422/38; 165/901; 165/902; 210/175; 210/179; 210/180; 422/1; 422/307; 422/308
[58] Field of Search .................................. 422/307, 308, 422/1, 38; 210/179, 175, 180; 165/901, 902

[56] References Cited

U.S. PATENT DOCUMENTS

| | | | |
|---|---|---|---|
| 2,190,598 | 2/1940 | Fischer | 210/2 |
| 2,613,180 | 10/1952 | Green et al. | 210/2 |
| 2,847,379 | 8/1958 | Spiegel et al. | 210/6 |
| 2,998,139 | 8/1961 | Novak | 210/97 |
| 3,296,122 | 1/1967 | Karassik et al. | 210/2 |
| 3,337,448 | 8/1967 | Rich | 210/3 |
| 3,535,234 | 10/1970 | Gilwood | 210/7 |
| 4,092,338 | 5/1978 | Tossey | 210/142 |
| 4,274,838 | 6/1981 | Dale et al. | 48/111 |
| 4,511,370 | 4/1985 | Hunziker et al. | 48/197 |
| 4,582,607 | 4/1986 | Kiese et al. | 210/612 |
| 4,668,391 | 5/1987 | Ottens | 210/181 |
| 4,925,571 | 5/1990 | Jacob et al. | 210/742 |
| 4,988,442 | 1/1991 | Highsmith et al. | 210/609 |
| 5,034,131 | 7/1991 | Steinroos et al. | 210/612 |
| 5,417,937 | 5/1995 | Voigt et al. | 422/189 |
| 5,433,844 | 7/1995 | Christy | 210/149 |
| 5,480,540 | 1/1996 | Day et al. | 210/181 |

FOREIGN PATENT DOCUMENTS

| | | |
|---|---|---|
| 0 034 872 | 9/1981 | European Pat. Off. . |
| 0 536 963 | 4/1993 | European Pat. Off. . |
| 24 10 323 | 9/1975 | Germany . |
| 10305300 | 11/1998 | Japan . |

*Primary Examiner*—Krisanne Thornton
*Attorney, Agent, or Firm*—Baker & Maxham

[57] ABSTRACT

A continuous flow sludge pasteurization system includes a flow chamber having an inlet and an outlet and structure within the liquid flow chamber between the inlet and the outlet defining a continuous path for maintaining a continuous flow of a slurry from the inlet toward the outlet at a predetermined rate for establishing a minimum period of residence time of the slurry within the flow chamber, the residence time sufficient to kill all pathogens in the slurry at a predetermined minimum temperature of between about 145 and 160 degrees F, a pump for introducing a continuous flow of a liquid slurry of sludge into the liquid flow chamber and for establishing and maintaining a continuous flow of a liquid slurry through the liquid flow chamber from the inlet to the outlet at the predetermined rate, and a source of heat for introducing heat into a liquid slurry being introduced into the liquid flow chamber for heating the continuous flow of slurry to the predetermined minimum temperature, and dewatering apparatus for removing substantial amounts of water from the slurry to produce a sludge. This system and process is designed to be an integral component of a water reclamation system and capable of meeting a variety of pathogen reduction requirements.

28 Claims, 4 Drawing Sheets

CONTINUOUS FLOW PASTEURIZATION OF SEWAGE SLUDGE

REFERENCE TO RELATED APPLICATION

This is as continuation-in-part of my application Ser. No. 08/792,692 filed Jan. 29, 1997, now U.S. Pat. No. 5,888,453.

BACKGROUND OF THE INVENTION

The present invention relates to the processing of sewage sludge and pertains particularly to improved method and apparatus for processing municipal sewage sludge for eliminating pathogens.

Densely populated areas of the world, such as cities, produce waste collected and treated as sewage that must be disposed of in a reasonably sanitary manner in order to protect public health. Most cities have sewer systems which collect and carry raw sewage, flushed by water to collection and treatment plants. The raw sewage is normally treated at various levels including anaerobic and/or aerobic digestion and sludge resulting from the treatment is disposed of in various manners including in land fills. A small percentage of it is disposed of on agricultural land. Disposal of the sludge is a problem because it contains all of the disease organisms common to man.

Raw sewage collected at sewage treatment plants is normally first subjected to a primary treatment by settling and screening to dispose of sand, grit and some soluble solids. The settled solids are undigested raw sludge and normally pumped to aerobic digester where the raw sludge is converted to an organically stable form. The settled sewage is subjected to secondary treatment, where microorganisms are introduced with an excess of oxygen utilizing aeration. This secondary treatment results in digestion of the settled solids, aerobically and/or anaerobically. The resulting solids and treatment additives are separated or settled out and the sludge is removed for further processing.

The material that settles out is digested to further stabilize organic matter in the sludge solids. This treated sludge is de-watered and the sludge is then typically disposed of by commercial processors who are paid by the treatment plant to dispose of the sludge. The commercial processors further treat the sludge by composting it so that it can then be used for fertilizer or soil amendment. This amounts to an enormous cost to the treatment plant.

In the past, much of the sludge has been used in land fills or has been dumped in the ocean. These means of disposal are no longer permitted because of health and environmental concerns. A considerable effort has been undertaken to provide appropriate means of disposing of sludge without harming the population or the environment. Many techniques have been proposed for treating raw sludge to allow for disposal, such as dewatering and subsequent incineration. However, incineration introduces its own problems, such as air pollution from the burning of the sludge.

Many efforts are underway to recover the sludge and use it as a resource for its nutrient value for land application as fertilizer or soil amendment. Proposals have been made, for example, for its use in desert land reclamation. However, pathogens in the sludge must be removed before its application in or near populated areas where it is likely to be contacted by humans or animals.

Present concerns for public health require that the sludge be further processed if it is to be used as a fertilizer or as a soil conditioner, such as in land rock reclamation projects. This further treatment is required because the typical sludge product of a treatment plant still contains substantial quantities of bacteria, viruses and other organisms. One method that has been proposed for eliminating this problem is that of pasteurization. However, this is a costly process requiring expensive plant and equipment and substantial amounts of energy to carry out. Heating the sludge to effectively pasteurize it requires that it be heated to a temperature of at least about 160° F. and maintained at that temperature for a minimum of 30 minutes. This is typically carried out in a batch process in large holding tanks to insure that no short circuiting occurs. Once the sludge has been pasteurized, it is suitable for land fills and land reclamation and low grade fertilizer. However, such pasteurization in this manner is expensive and not cost effective.

Presently known processes for pasteurization, however, are batch processes and are enormously expensive to construct and operate. Pasteurization, however, can ultimately reduce some cost of disposal by reducing the expense of paying commercial disposal companies for disposal of the sludge. Pasteurization can turn the sludge into a resource making it sufficiently desirable that much of the cost can be recovered. However, the pasteurization costs must be sufficiently low to make the whole operation economical.

The system in accordance with the parent application has proven satisfactory. However, I have discovered certain improvements which make it more economical.

It is therefore desirable that an inexpensive and cost-effective pasteurization system and process be available.

SUMMARY AND OBJECTS OF THE INVENTION

It is the primary object of the present invention to provide a method and apparatus for continuous processing and pasteurization of sewage.

In accordance with the primary aspect of the present invention, a continuous process pasteurization system comprises a liquid flow chamber having an inlet and an outlet and defining a continuous liquid flow path for maintaining a continuous flow of a slurry from said inlet toward said outlet at a predetermined rate for establishing a minimum period of residence time of the slurry within said flow chamber sufficient to kill all pathogens in said slurry at a predetermined minimum temperature of between about 145 and 160 degrees F, means for introducing a continuous flow of a liquid slurry of sludge into said liquid flow chamber and for establishing and maintaining a continuous flow of a liquid slurry through said liquid flow chamber from said inlet to said outlet at said predetermined rate, and means for introducing heat into a liquid slurry being introduced into said liquid flow chamber for heating said continuous flow of slurry to said predetermined minimum temperature, and dewatering means for removing a substantial amount of water from said sludge.

BRIEF DESCRIPTION OF THE DRAWINGS

The above and other objects and advantages of the present invention will become apparent from the following description when read in conjunction with the accompanying drawings wherein.

DETAILED DESCRIPTION OF PREFERRED EMBODIMENTS

Figure 1:
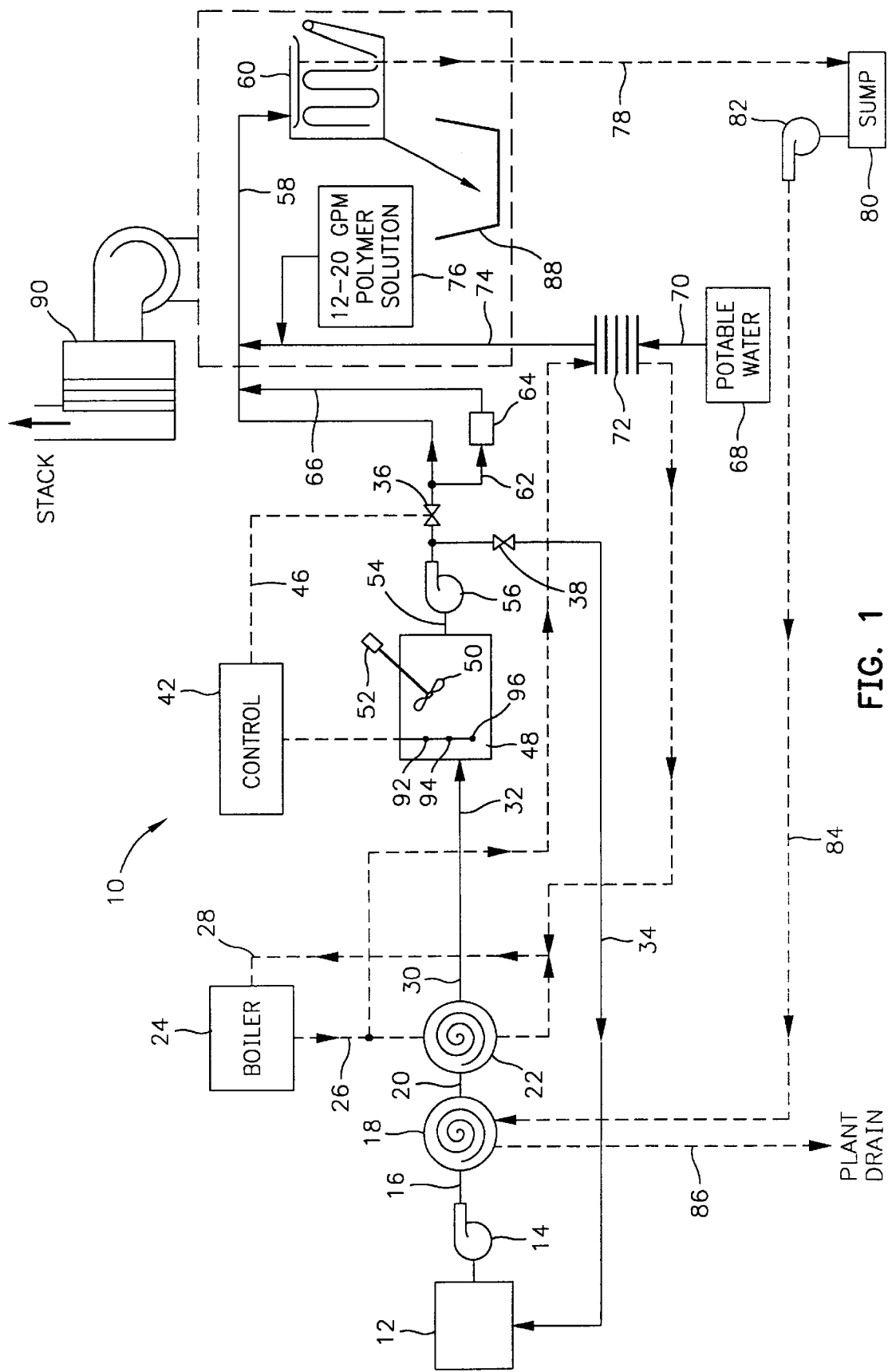
FIG. 1 is a schematic illustration of a system in accordance with a preferred embodiment of the present invention.

The present invention was devised to provide a system to enable sewage to be economically treated and disposed of. The system provides a continuous flow pasteurization of sludge to eliminate pathogens so that the sludge may be used for fertilizer and/or soil amendment. Referring to FIG. 1 of the drawings, a system in accordance with the present invention is schematically illustrated and designated generally by the numeral 10. The system is shown embodied in a treatment plant which comprises a source of sludge such as an underground sludge holding tank 12 which receives sludge from a treatment plant such as an anaerobic/aerobic digester. The sludge is typically a slurry of solids in the range of about two to about seven percent (2–7%) in water as a carrier. The percept of solids is limited by what can be pumped through the system and can vary from one-half of one percent up to about ten percent (0.5–10%) depending on the pump and other portions of the system. A pump 14 delivers a slurry of the sludge by way of a line 16 to a first heat exchanger 18 where it is heated to a first temperature. The sludge is then pumped by a conduit or line 20 to a second heat exchanger 22 where it is heated to the pasteurization temperature of about 140 to about 160 degrees Fahrenheit.

The first heat exchanger 18 is a preheater which receives its heat by way of extruded water from the plant dewatering process, as will be explained. The second heat exchanger 22 receives heat from hot water from a boiler 24 by way of lines or conduits 26. The heat supplied in the present system is by way of water at 180° F. for raising the temperature of sludge in the heat exchanger 22 to preferably about 160° F. Hot water from the heat exchanger 22 recirculates by way of line 28 back to the boiler 24 for reheating. The heat exchangers may be any suitable type through which sludge can pass and can transfer heat from water or steam to the sludge. Applicant has found spiral heat exchangers of the type available from Alfa-Lavel Thermal, Inc. to be particularly suitable in one embodiment of the invention.

The heated sludge which is preferably a slurry of anywhere from about two to seven percent (2–7%) solids in water is maintained at a sufficient temperature, preferably about 160° F, for a period of time, preferably about thirty minutes, to kill all pathogens in the slurry. The system is constructed and/or configured to provide a continuous flow system to maintain a continuous flow of the slurry from an inlet to an outlet at a pre-determined elevated temperature for a period of time sufficient to kill the pathogens in the slurry. As illustrated, the slurry flows by way of a line or conduit 30 to a detention tank or circuit 48 where it is maintained at about 160° F. for about thirty minutes. The slurry is then pumped by pump 56 from the detention circuit via conduit 58 which includes a junction with recirculating line 34, controlled by temperature responsive valves 36 and 38, which operate, if necessary, to recirculate the sludge slurry back through the heat exchanger. Recirculation may be necessary to ensure that it reaches and maintains the desired or predetermined pasteurization temperature of about 160° F. prior to sludge dewatering. When the sludge reaches the juncture of lines 58 and 34, sensors sense the temperature by way of conductors 46 at control system or panel 42 which monitors the temperature and operates valves 36 and 38 to recirculate the slurry, if necessary. These valves and sensors may be positioned at the inlet to the tank 48 to insure the proper temperature prior to flowing into the tank. If the temperature of the sludge is less than the predetermined minimum temperature, valve 36 closes and valve 38 opens to recirculate the sludge back to the intake to pump 14 where it is again passed through the heat exchanger 22 for further heating. The recirculating line can be either upstream or downstream of the detention tank or it can have both. However, in the preferred arrangement, it is downstream to ensure that all material passing through the detention tank has been maintained at the minimum required temperature for the required time.

When the sludge reaches a suitable temperature above its predetermined minimum pasteurization temperature in heat exchanger 22, it passes by way of conduit or line 32 into the detention circuit 48 which in the illustrated embodiment is a vertical tank having a mixing or stirring paddle or propeller 50 positioned between the inlet and the outlet driven by a suitable motor 52. The slurry enters the detention tank 48 at one side or end and preferably at the bottom thereof from line 32 and flows or migrates in the tank toward the top or outlet for its thirty minute holding period until it reaches the top of the tank. The rotating propeller 50 assures suspension of the biosolids and acts against the flow of sludge toward the outlet and thereby prevents short circuiting by forcing the slurry to take a long path around the propeller. When the slurry reaches the top or opposite side of the tank it passes out of the tank by way of conduit or pipe 54 to the inlet of pump 56 for further processing such as delivery to a dewatering system. The temperature of the slurry is checked at this point and recirculate back to heat exchanger 22 if necessary, to ensure its pasteurization temperature and period.

The detention tank system as illustrated has been proven by extensive testing to hold the slurry for the necessary minimum pasteurization time without short circuiting. In other words no unpasteurized slurry has been found to pass through the tank during these tests in normal operation. This has been validated through extensive fecal Cominform, enteric virus, and helminth ova testing. Alternative detention systems or circuits such a baffled tank or an elongated circuitous pipe may be used to provide further insurance if desired. It will be appreciated that the sludge can be raised to a much higher temperature for a shorter time and achieve pasteurization. However, higher temperatures would require more energy resulting in higher costs and in most instances would not be economical.

The pump 56 delivers the pasteurized slurry by way of line 58 to a suitable dewatering system 60, where a large percentage of the water is removed to provide a pathogen free sludge. It will be appreciated that any number of different suitable dewatering systems are available and may be utilized. The dewatering system of the present system is illustrated as a belt filter press however, it may be a centrifuge or any other suitable system. Alternatively, the pasteurized sludge or slurry is fed by way of a conduit 62 to a second anaerobic digester 64 where it is further digested and then passed by outlet line 66 to line 58 where it is then conveyed to the dewatering system 60.

A quantity of polymer is fed in solution such as in water from a source of water 68 by a conduit 70 to a heat exchanger 72 and a line 74. Polymer with a mix of 12–20 gal/min is fed from a source 76 into the conduit 58 for introduction and mixing with the sludge before it enters into the dewatering apparatus 60. This aids in the dewatering of the sludge.

The dewatering apparatus 60 is preferably a belt type filter press which presses the sludge between belts and rollers, collects and returns the extracted water by way of a conduit 78 to pump 80. This water is circulated by way of pump 82 in conduit 84 back to the preheater 18 to recover some heat from the water before it is discharged by way of conduit 86 for reclamation. This water is returned to the plant influent for processing to remove organic and nitrogen compounds.

The pasteurized sludge cake recovered from the dewatering apparatus 60 passes into a suitable storage bin or reservoir 88 for retrieval and disposal. The sludge forms a cake that is composed of 20–22% dry solids. The sludge cake is then, because of its pasteurization, completely devoid of pathogens and can now be distributed for agricultural purposes, such as fertilizer and/or soil conditioning. The sludge is maintained in the detention circuit 48 at a temperature of about 160° F. for a time of about 30 minutes to kill the bacteria and viruses therein. This system has been pilot tested and proven reliable and found to produce Class A biosolids, which is defined as free of pathogens. This system and process can be used to satisfy U.S. EPA Part 503 Regulations which define pasteurization of biosolids as that which are maintained at a 158° F. or higher, for at least 30 minutes.

The present pasteurization process has been tested and shown to produce Class A biosolids when heated to and maintained at about 160° F. temperature for a detention time of 30 minutes. Pilot testing results indicate Class A biosolids can be achieved at lower temperatures and detention times. Thus, pathogen-free Class A biosolids can be produced in the system of the present invention with very flexible operating parameters. This flexibility enables the parameters of operation to be adjusted for the most economical operation. The system provides a continuous flow processing system that can be built into sewage treatment plants for a continuous flow 24 hour per day continuous operation.

This system also provides a highly efficient economical operation for sewage treatment that produces Class A biosolids that can be disposed off without further processing, such as the traditional methods of composting. The system also removes much of the sulphur and other odor-causing components from the system at the dewatering operation with suitable scrubber system 90. Thus, it produces an environmentally compatible system. The system can be set up to operate automatically with the controller 42 having temperature monitoring means at strategic positions in the system, such as a plurality of sensors 82, 84 and 86, in the detention tank or circuit 48. The present system can be modified in a number of ways to produce the above described desired results.

The conversion of biosolids to class A increases their marketability and eliminates the management and site restrictions associated with class B materials. This process has also been found to enhance the dewatering process enabling the removal of a higher percentage of the water. This reduces the cost of transportation of the resulting biosolids product.

Figure 2:
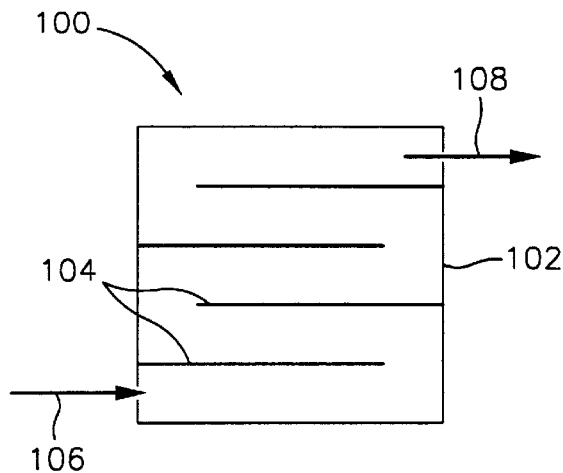
FIG. 2 is a diagrammatic illustration of an alternate embodiment of the pasteurization circuit.

Referring to FIG. 2, an alternate embodiment of the detention circuit is illustrated and designated generally by the numeral 100. This may take any number of suitable forms, but in the illustrated embodiment a reservoir 102 is provided with a plurality of baffles or walls 104 providing a circuitous or tortuous path from an inlet 106 to an outlet 108. This path would have a length sufficient that the slurry of sludge would maintain residence within the circuit for the predetermined necessary minimum time at the prescribed flow-rate. The slurry is forced to follow the entire path to the outlet, and ensures that no short-circuiting of the temperature residence time occurs.

Figure 3:
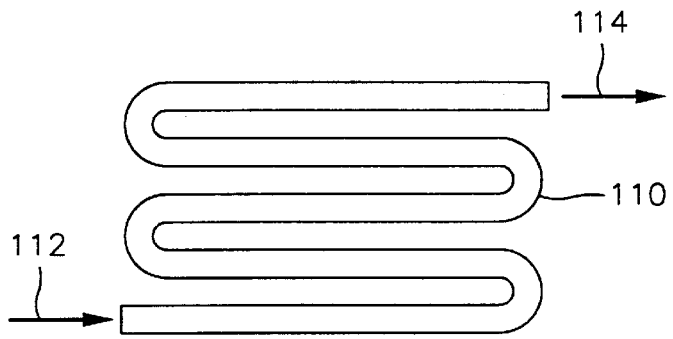
FIG. 3 is a diagrammatic illustration of a another embodiment of a pasteurization circuit.

Referring to FIG. 3, a further embodiment of the detention circuit is illustrated and comprises an elongated pipe or conduit 110 having an inlet 112 and an outlet 114 and forming a path of sufficient length to insure the required residence time for the selected temperature. The conduit forms a circuitous path from the inlet 112 to the outlet 114. While the path is illustrated as being serpentine, it may be straight or have other curvatures including circular or spiral (not shown). This path would have a length sufficient that the slurry of sludge would maintain residence within the circuit for the predetermined necessary minimum time at the prescribed flow-rate. The slurry is forced to follow the entire path to the outlet, and ensures that no short-circuiting of the temperature residence time occurs. These two embodiments may also be provided with suitable stirring means, if necessary, to insure that the solids remain in suspension.

Figure 4:
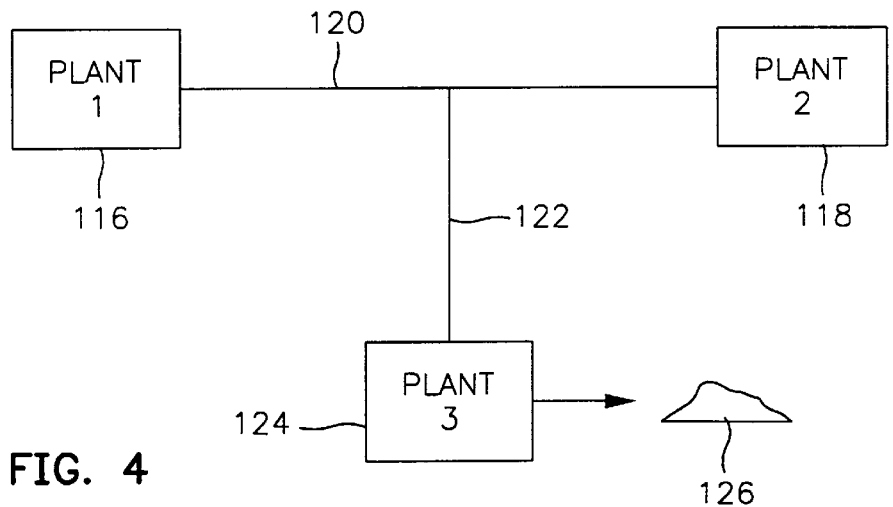
FIG. 4 is a schematic diagram illustrating a multi-plant processing system.

Referring to FIG. 4, a multiple plant system is illustrated wherein a plurality of plants 116 and 118 supply slurry from their digesters via pipelines 120 and 122 to a plant 124 having a continuous pasteurization system. The plant 124 processes the sludge to produce class A sludge that can be economically disposed of. This system provides an arrangement for a metropolitan water district having a number of small wastewater treatment plants to invest in a single pasteurization system in accordance with the present invention. The pasteurization system can operate in a continuous flow process around the clock and provide improved economy for the entire district.

Figure 5:
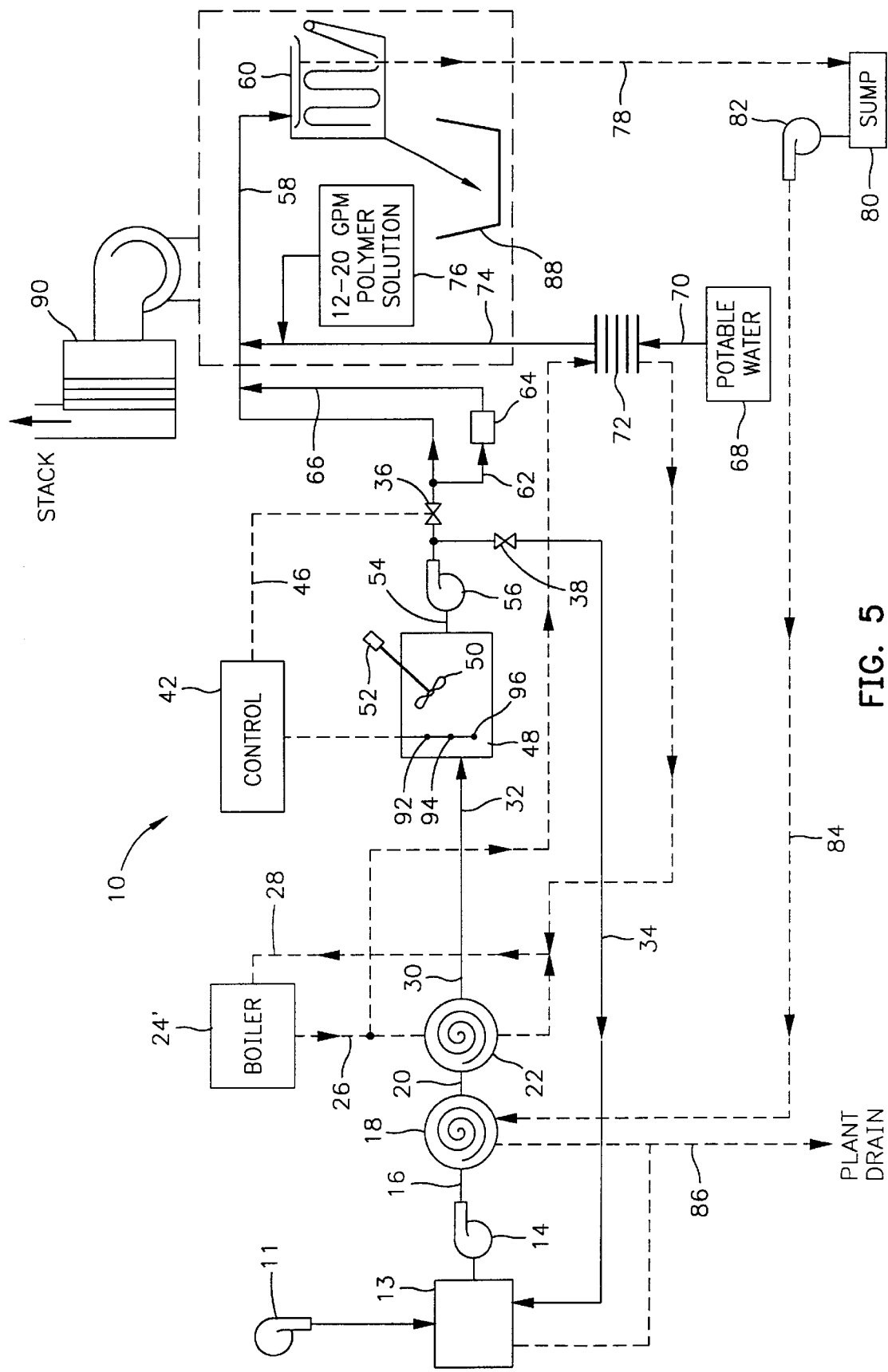
FIG. 5 is a schematic illustration of an further embodiment of the pasteurization circuit.

Referring to FIG. 5, a modification of a plant as illustrated in FIG. 1 is shown wherein a like numbers identify the same elements and similar or equivalent elements are identified by the numeral primed. This system is provided with suitable means 13 to thicken the slurry by increasing the percentage of solids content. Any suitable dewatering apparatus that does not interfere with the continuous flow of the system can be used for this purpose. A typical slurry is supplied from a source such as a digester or other source represented by a pump 11 to the thickener or dewatering unit 13. The slurry may contain from as low as about one-half or one percent or less up to as much as five percent of solids and water is removed to increase the solids content up to about 6.0% or in some instances up to as much as 10.0%. This removes anywhere from sixty to ninety percent of the water content and considerably reduces the amount of heat required to raise the temperature of the slurry to the pasteurization temperature. This reduction in heat and energy results improved efficiency and reduced costs. The water content can be reduced to the minimum amount necessary to still enable it to flow through the treatment chamber and other components of the circuit of the system. A suitable apparatus for this task is a dewatering apparatus sold under the trademark Aqua Belt by the Ashbrook Corp., of Houston, Tex.

Figure 6:
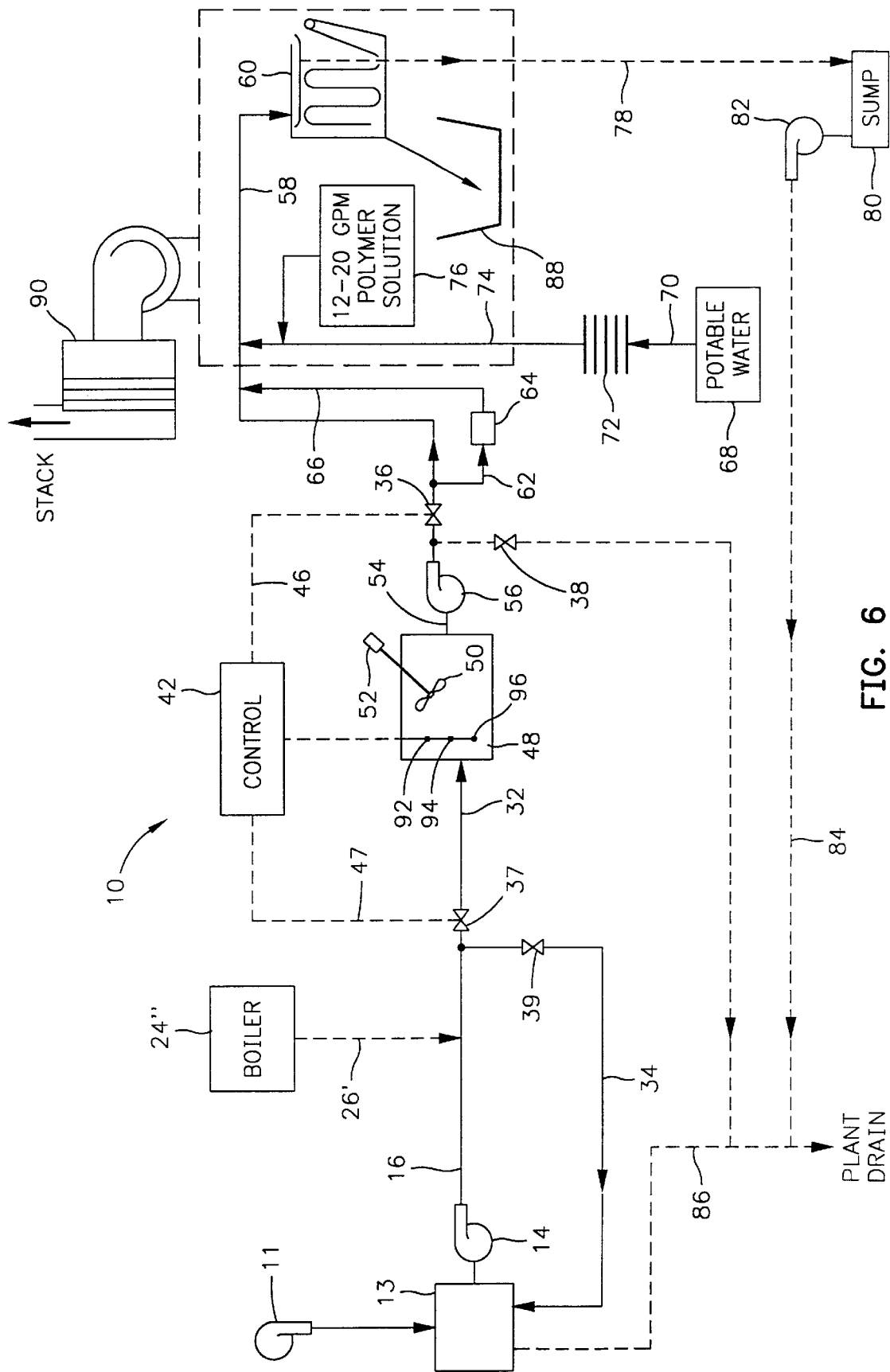
FIG. 6 is a schematic illustration of still another embodiment of the pasteurization circuit.

Referring to FIG. 6, a further embodiment is illustrated wherein the slurry is heated to the desired temperature by direct injection of live steam. As illustrated, the heat exchanger of prior embodiments have been omitted, and live steam from a boiler is injected directly into the slurry such as via line 16'. A pump 11 supplies slurry to a dewatering unit 13 which reduces the water content so that the solids is at a maximum percent that can be passed through the system. This can be up to about 10% with direct injection and the heat exchangers removed. The slurry is pumped via line 16' into the tank 48 as live steam is injected into the slurry to raise the temperature up to a suitable value. The steam may be injected into the slurry prior to its introduction into tank 48 or it may be injected into the slurry in the tank so long as the necessary flow through time can be maintained. In a preferred arrangement, the steam is injected prior to introduction of the slurry into the tank 48. In this embodiment recycling of the slurry to further raise its temperature, if needed, is controlled by valves 37 and 39 which may be provided prior to tank 48. This insures that slurry of insufficient temperature is returned to a position up stream of the steam injection to reheat the slurry to the proper temperature. Temperature sensing and control of valve is by way of a suitable control line such as a conductor 47.

While I have illustrated and described my invention by means of specific embodiments, it is to be understood that numerous changes and modifications may be made therein without departing from the spirit and scope of the invention, as defined in the appended claims.

I claim:

1. A continuous flow sludge pasteurization system, comprising:
    a liquid flow chamber having an inlet and an outlet and defining a continuous liquid flow path for maintaining a continuous flow of a slurry from said inlet toward said outlet at a predetermined rate for establishing a minimum period of residence time of the slurry within said flow chamber sufficient to kill all pathogens in said slurry at a predetermined minimum temperature of between about 145 and 160 degrees F;
    means for introducing a continuous flow of a liquid slurry of sludge into said liquid flow chamber and for establishing and maintaining a continuous flow of a liquid slurry through said liquid flow chamber from said inlet to said outlet at said predetermined rate; and
    means for introducing heat into a liquid slurry being introduced into said liquid flow chamber for heating said continuous flow of slurry to said predetermined minimum temperature.

2. The system of claim 1 further comprising first dewatering means for receiving said slurry from said outlet for removing water from said slurry.

3. The system of claim 2 wherein said liquid flow chamber comprises a rotating propeller disposed between said inlet and said outlet and acting against the of flow of said slurry toward said outlet.

4. The system of claim 3 wherein said for introducing heat is a spiral heat exchanger.

5. The system of claim 3 wherein said heat exchanger includes a pre-heater.

6. The system of claim 3 further comprising second dewatering means at said inlet for increasing the solids content of said slurry to within a range of from about five to about ten percent.

7. The system of claim 1 further comprising dewatering means at said inlet for increasing the solids content of said slurry to within a range of from about five to about ten percent.

8. The system of claim 7 further comprising means for selectively recirculating said slurry to said heat exchanger for obtaining said minimum predetermined temperature.

9. The system of claim 1 further comprising means for selectively recirculating said slurry to said heat exchanger for obtaining said minimum predetermined temperature.

10. The system of claim 9 further comprising a second stage anaerobic digester down stream of said liquid flow chamber.

11. The system of claim 1 further comprising a second stage anaerobic digester down stream of said liquid flow chamber.

12. The system of claim 1 wherein said liquid flow chamber is an elongated conduit formed in a circuitous path between an inlet and an outlet thereof.

13. The system of claim 1 wherein said liquid flow chamber is a reservoir having an inlet at one end thereof and an outlet at another end, and a series of baffles between said inlet and said outlet forming an elongated circuitous path between said inlet and said outlet thereof.

14. A continuous flow sludge pasteurization system, comprising:
    a liquid flow system including a continuous flow chamber having an inlet and an outlet;
    means for introducing and maintaining a continuous flow of a slurry into said inlet and through continuous flow chamber out said outlet;
    a source of heat for supplying heat to said slurry at said inlet for heating said slurry to a predetermined minimum temperature of about one hundred forty-five to about sixty degrees Fahrenheit;
    flow constraining means within said continuous flow chamber positioned between said inlet and said outlet constraining the flow of said slurry toward said outlet for maintaining said slurry in circulation in said reservoir at said predetermined temperature for a minimum period of about thirty minutes sufficient to kill all pathogens in said slurry;
    first dewatering means at said inlet for receiving said slurry and removing water from said slurry for increasing the solids content thereof up to about ten percent; and
    second dewatering means for receiving said slurry from said outlet and removing water from said slurry.

15. The system of claim 14 wherein said continuous flow chamber is a reservoir having an inlet at one end thereof and an outlet at another end thereof.

16. The system of claim 15 wherein said flow constraining means comprises a rotating propeller acting against the flow of said slurry from said inlet toward said outlet.

17. The system of claim 14 wherein said source of heat exchanger is a steam injector for direct injection of steam into said slurry.

18. The system of claim 14 wherein said first dewatering means comprises a belt filter press.

19. The system of claim 18 further comprising a second stage anaerobic digester down stream of said continuous flow chamber.

20. The system of claim 14 wherein said continuous flow chamber is a reservoir having an inlet at the bottom thereof and an outlet at the top, and a series of baffles between said inlet and said outlet forming an elongated circuitous path between said inlet and said outlet thereof.

21. A continuous flow of sludge pasteurization process, comprising:
    providing a continuous flow circuit having an inlet and an outlet;
    introducing a continuous flow of a liquid slurry into said circuit at said inlet;
    heating said slurry to a predetermined minimum temperature of from about one hundred forty-five to about one hundred sixty degrees Fahrenheit;

maintaining said continuous flow of slurry in said circuit at said predetermined temperature for a minimum period of about thirty minutes sufficient to kill all pathogens in said slurry while maintaining a continuous flow of said slurry from said outlet; and removing water from said slurry to produce a sludge.

22. The process of claim 21 wherein said step of introducing a continuous flow of a liquid slurry includes the step of reducing the water content of said slurry up to about ninety percent.

23. The process of claim 21 wherein said step of introducing a continuous flow of a liquid slurry includes the step of increasing the solids content of said slurry to within a range of from about five to about ten percent.

24. The process of claim 23 wherein the step of heating said slurry includes direct injection of steam into said slurry.

25. The process of claim 23 wherein said step of introducing heat includes introducing said heat via a spiral heat exchanger.

26. The process of claim 22 wherein said step removing water from said slurry to produce a sludge is carried out by means of a belt filter press.

27. The process of claim 22 further comprising the step of circulating said slurry through an anaerobic digester prior to said dewatering step.

28. The process of claim 22 wherein said step of providing a continuous flow circuit includes the steps of:

providing a reservoir having an inlet and an outlet; and providing a rotating propeller positioned between said inlet and said outlet and acting against the flow of said slurry toward said outlet.

* * * * *